United States Patent
Belanoff

(10) Patent No.: US 8,476,254 B2
(45) Date of Patent: Jul. 2, 2013

(54) METHODS FOR TREATING PSYCHOSIS ASSOCIATED WITH INTERFERSON-α THERAPY

(75) Inventor: Joseph K. Belanoff, Woodside, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 2389 days.

(21) Appl. No.: 10/519,008

(22) PCT Filed: Jul. 2, 2003

(86) PCT No.: PCT/US03/21245
§ 371 (c)(1),
(2), (4) Date: Dec. 21, 2004

(87) PCT Pub. No.: WO2004/004653
PCT Pub. Date: Jan. 15, 2004

(65) Prior Publication Data
US 2006/0063748 A1    Mar. 23, 2006

Related U.S. Application Data

(60) Provisional application No. 60/393,660, filed on Jul. 2, 2002.

(51) Int. Cl.
| | |
|---|---|
| A61K 31/00 | (2006.01) |
| A61K 31/56 | (2006.01) |
| A61K 31/5685 | (2006.01) |
| A61K 31/569 | (2006.01) |
| A61K 31/70 | (2006.01) |
| A61K 38/00 | (2006.01) |
| A61K 38/21 | (2006.01) |
| A61P 25/18 | (2006.01) |

(52) U.S. Cl.
USPC ............. 514/179; 514/4.3; 514/17.5; 514/43; 514/894; 424/85.4; 424/85.7

(58) Field of Classification Search
USPC ................. 424/85.4, 85.7; 514/4.3, 17.5, 43, 514/179, 894
See application file for complete search history.

(56) References Cited

U.S. PATENT DOCUMENTS

| | | | | |
|---|---|---|---|---|
| 6,150,349 A | * | 11/2000 | Schatzberg et al. | 514/179 |
| 6,340,696 B1 | | 1/2002 | Camden | |
| 6,649,644 B1 | * | 11/2003 | Korant | 514/405 |
| 2002/0111362 A1 | * | 8/2002 | Rubinfeld | 514/283 |

FOREIGN PATENT DOCUMENTS

| | | |
|---|---|---|
| WO | WO 96/36351 A1 | 11/1996 |
| WO | WO 98/24451 A1 | 6/1998 |
| WO | WO 00/32177 A2 | 6/2000 |
| WO | WO 01/81359 A1 | 11/2001 |

OTHER PUBLICATIONS

Bozikas et al., A interferon-alpha-induced psychotic disorder in a patient with chronic hepatitis C, 2001, European Psychiatry, 16, 136-137.*
Ademmer et al., Suicidal Ideation with IFN- α and Ribavirin in a Patient with Hepatitis C, Psychosomatics 42:4, 365-367, 2001.*
Dieterich, Treatment of Hepatitis C and Anemia in Human Immunodeficiency Virus-Infected Patients, The Journal of Infectious Diseases, 185(Suppl 2):S128-37, 2002.*
Abstract, Shimizu et al, Increase in serum interleukin-6, plasma ACTH and cortisol levels after systemic interferon-α administration, Endocrine Journal, 42(4):551-6, 1995.*

* cited by examiner

*Primary Examiner* — James H. Alstrum-Acevedo
(74) *Attorney, Agent, or Firm* — Kilpatrick Townsend & Stockton LLP

(57) ABSTRACT

The present invention relates to the treatment of psychosis associated with interferon-α therapy by administering an amount of a glucocorticoid receptor antagonist effective to ameliorate the symptoms of psychosis in the patient, wherein the patient is not otherwise in need of treatment with a glucocorticoid receptor antagonist. The present invention further relates to kits for the treatment of Hepatitis C infection in a patient.

19 Claims, No Drawings

METHODS FOR TREATING PSYCHOSIS ASSOCIATED WITH INTERFERSON-α THERAPY

FIELD OF THE INVENTION

The present invention relates to the treatment of psychosis associated with interferon-α therapy. The present invention further relates to kits for the treatment of Hepatitis C in a patient.

BACKGROUND OF THE INVENTION

Interferon-α has proven to be an effective therapy for a variety of diseases, including hepatitis, chronic myelogenous leukemia, cancers, and HIV. In particular, interferon-α has proven to be a useful therapy for Hepatitis C. Hepatitis C is regarded as a major public health concern with over 4 million affected individuals in the U.S. alone, (Alter, C. *Hepatology*, 26, 62S-65S (*supplement*)). The only treatment presently approved by the FDA for Hepatitis C treatment is interferon-α, which is typically used in combination with the synthetic purin nucleoside analogue, ribavirin. Interferon-α alone, and in combination with ribavirin, successfully reduces viral load and elevated liver transaminases. However, despite the successes of interferon-α treatment, interferon-α is used cautiously as it is associated with severe side effects, including psychosis (Koshy et al. *J. Clin. Gastroenterol.* 35(1):82-5 (2002), Verbaan et al., *Eur. J. Gastroenterol Hepatol.*, 14(6): 627-633 (2002), Bean, *Am Clin Lab.*, 21(3):18-20 (2002), Kraus et al., *Alimentary Pharmacology & Therapeutics*, 16(6):1091 (2002), Kjaergard et al., *Cochrane Database Syst. Rev*, (2002), Rajender et al., *Adv Drug Deliv Rev.*, 54(4):571-586 (2002)).

Interferon α therapy has other common side effects such as flu-like symptoms including chills, fever, malaise, muscle pain, and anorexia. However, it is the neuropsychiatric side effects such as severe depression and psychosis that usually force withdrawal from interferon α therapy.

For the first time, the present inventors have discovered that patients suffering from psychosis associated with interferon-α treatment can be effectively treated with antiglucocorticoid medications. Given the prevalence of interferon-α treatment for hepatitis C and other diseases, there exists a need for eliminating, reducing, or treating the side effects associated with interferon-α therapy. The present invention meets this and other needs.

SUMMARY OF THE INVENTION

It has now been discovered that antiglucocorticoids can be used for the treatment of interferon-α associated psychosis. Accordingly, the present invention provides a method of ameliorating the symptoms of psychosis associated with interferon-α therapy in a patient by administration of an amount of a glucocorticoid receptor antagonist effective to ameliorate the symptoms of psychosis in the patient, with the proviso that the patient is not otherwise in need of treatment with a glucocorticoid receptor antagonist.

In one embodiment, the glucocorticoid receptor antagonist comprises a steroidal skeleton with at least one phenyl-containing moiety in the 11-beta position of the steroidal skeleton. In another embodiment, the phenyl-containing moiety in the 11-beta position of the steroidal skeleton is a dimethylaminophenyl moiety. In a preferred embodiment, the glucocorticoid receptor antagonist comprises mifepristoneIn another embodiment, the glucocorticoid receptor antagonist is selected from the group consisting of 11-β-(4-dimethylaminoethoxyphenyl)-17α-propynyl-17β-hydroxy-4,9-estradien-3-one, and 17β-hydrox-17α-19-(4-methyl-phenyl)androsta-4,9 (11)-dien-3-one.

In one embodiment, the glucocorticoid receptor antagonist is selected from the group consisting 4α(S)-Benzyl-2(R)-prop-1-ynyl-1,2,3,4,4α,9,10,10a(R)-octahydro-phenanthrene-2,7-diol and 4α(S)-Benzyl-2(R)-chloroethynyl-1,2,3,4,4α,9,10,10a(R)-octahydro-phenanthrene-2,7-diol. In an alternative embodiment, the glucocorticoid receptor antagonist is (11β,17β)-11-(1,3-benzodioxol-5-yl)-17-hydroxy-17-(1-propynyl)estra-4,9-dien-3-one.

In one embodiment, the glucocorticoid receptor antagonist is administered to the patient concomitantly with interferon-α. In another embodiment, the glucocorticoid receptor antagonist is administered to the patient throughout the course of interferon-α therapy. In a preferred embodiment, the glucocorticoid receptor antagonist is administered to the patient concomitantly with interferori-α and a second therapeutic agent. In another embodiment, the second therapeutic agent is an anti-viral agent. In a related embodiment, the anti-viral agent is ribavarin.

In one embodiment, the glucocorticoid receptor antagonist is administered in a daily amount of between about 0.5 to about 25 mg per kilogram of body weight per day. In another embodiment the glucocorticoid receptor antagonist is administered in a daily amount of between about 1 to about 4 mg per kilogram of body weight per day.

In one embodiment the mode of administration is selected from the group consisting of oral administration, transdermal application, nebulized suspension, and aerosol spray. In another embodiment, the patient is suffering from a viral infection caused by a virus selected from the group consisting of hepatitis C virus, hepatitis B virus, and hepatitis D virus. In another embodiment, the patient is suffering from chronic myelogenous leukemia, HIV, Human T-Cell Lymphotropic Virus or cancer. In another embodiment, the patient has a history of substance abuse.

The invention also provides akit for treating a human infected with hepatitis C virus, the kit comprising, interferon-α, a specific glucocorticoid receptor antagonist; and, instructional material teaching the indications, dosage and schedule of administration of the glucocorticoid receptor antagonist and interferon-α to a patient suffering from hepatitis C infection. In one embodiment the kit further comprises a second therapeutic agent. In a preferred embodiment the the glucocorticoid receptor antagonist provided in the kit is mifepristone.

Definitions

The term "ameliorating the symptoms of psychosis associated with interferon-α therapy in a patient" means preventing the symptoms of psychosis associated with interferon-α therapy from occurring in a patient that is being treated with interferon-α but does not yet experience or exhibit symptoms of psychosis (prophylactic treatment), inhibiting the symptoms of psychosis (slowing or arresting the development of symptoms), providing relief from the symptoms or side-effects of psychosis (including palliative treatment), or relieving the symptoms of psychosis (causing regression of the symptoms of psychosis). The treatment or amelioration of symptoms can be based on objective or subjective parameters; including the results of a physical examination, neuropsychiatric exams, and/or a psychiatric evaluation.

The term "psychosis" or "psychotic" refers to a psychiatric symptom, condition or syndrome in its broadest sense, as defined in the DSM-IV (see fourth edition of Diagnostic and Statistical Manual of Mental Disorders (1994) Task Force on DSM-IV, American Psychiatric Association ("DSM-IV"); Kaplan, Ed. (1995) Comprehensive Textbook of Psychiatry/ VI, vol. 1, sixth ed., pp 621-627, Williams & Wilkins, Balt., Md.) comprising a "psychotic" component, as broadly defined above. The term psychosis can refer to a symptom associated with a general medical condition, a disease state or other condition, such as a side effect of drug abuse (a substance-induced disorder) or as a side effect of a medication, e.g., interferon-α Psychosis is typically defined as a mental disorder or condition causing gross distortion or disorganization of a person's mental capacity, affective response, and capacity to recognize reality, communicate, and relate to others to the degree of interfering with his capacity to cope with the ordinary demands of everyday life. "Psychosis associated with interferon-α therapy" refers to a psychosis that is induced by interferon-α therapy and is not associated with depression. Thus, "psychosis associated with interferon-α therapy" includes psychotic disorders associated with interferon-α treatment, but not psychotic disorders associated with depression, as in for example, psychotic major depression.

The phrase "not otherwise in need of treatment with a glucocorticoid receptor antagonist" means that a patient is not suffering from any condition known in the art to be effectively treatable with glucocorticoid receptor antagonists. Conditions known in the art to be treatable with glucocorticoid receptor antagonists include: psychotic major depression, dementia, stress disorders, diabetes, rheumatoid arthritis, autoimmune disease, HIV infection, dermatitis, inflammation, fibromyalgia, central nervous system disease, neurodegeneration, neural injuries, pelvic pain, and various cancers.

The term "Interferon-α," or "Interferon alpha," or "Interferon alfa" refers to a class of interferons with significant antiviral activity. Interferon-α-compounds are known in the art (see Goodman and Gilman's, The Pharmaceutical Basis of Therapeutics, Ninth Edition). Typically, clinically used recombinant alpha interferons are nonglycosylated proteins of approximately 17.5-21.5 kDa Examples include interferon-α-2a and interferon-α-2b.

The term "cortisol" refers to a family of compositions also referred to hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4dimethylaminophenyl) 17-beta-hydroxy-17-alpha-(1-propynyl)-estra-4,9-dien-3-one), or analogs thereof, which bind to the GR, typically with high affinity, and inhibit the biological effects initiated/mediated by the binding of any cortisol or cortisol analogue to a GR receptor. Chemical names for RU-486 vary, for example, RU486 has also been termed: 11β-[p-(Dimethylamino)phenyl]17β-hydroxy-17-(1-propynyl)-estra-4,9-dien-3-one; 11β-(4-dimethyl-aminophenyl)-17β-hydroxy-17α-(prop-1-ynyl)-estra-4,9-dien-3-one;17β-hydroxy-11β-(4-dimethylaminophenyl-1)-17α-(propynyl-1)-estra-4,9-diene-3-one; 17β-hydroxy-11β-(4-dimethylaminophenyl-1)-17α-(propynyl-1)-E; (11β,17β)-11-[4-dimethylamino)-phenyl]-17-hydroxy-17-(1-propynyl)estra-4,9-dien-3-one; and 11β-[4-(N,N-dimethylamino) phenyl]-17α-(prop-1-ynyl)-D-4,9-estradiene-17β-ol-3-one.

The term "specific glucocorticoid receptor antagonist" or "antiglucocorticoid" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" also refers to any composition or compound which inhibits any biological response associated with the binding of a GR to an agonist. By "specific", we intend the drug to preferentially bind to the GR rather than the mineralcorticoid receptor (MR) at a rate of at least 100-fold, and frequently 1000-fold.

An "antiglucocorticoid therapy" refers to administration of antiglucocorticoids to a patient.

The phrase "an amount of a glucocorticoid receptor antagonist effective to ameliorate the symptoms of psychosis in the patient", refers to the amount of the antiglucocorticoid that is will necessary to effect an amelioration of the symptoms of psychosis in a patient Amelioration of the symptoms of psychosis will be evidenced by an improved mental well-being of the patient. Improvement can be measured both before and after treatment with the anti-glucocorticoid by any method for assessing and diagnosing psychosis, as is described more fully below.

"Concomitant administration" of a drug, e.g., interferon-α, with a glucocorticoid blocker refers to administration of the drug and the glucocorticoid blocker at such times that both the drug and glucocorticoid blocker can reach a therapeutically effective amount. Such concomitant administration may involve concurrent (i.e. at the same time), prior or subsequent administration of the drug with respect to the administration of a glucocorticoid blocker. The precise timing of administration will depend on the relative onset of action and the half-lives of the drug and the particular glucocorticoid blocker chosen. A person of ordinary skill in the art, having knowledge of the drug to be administered and of glucocorticoid blockers, would have no difficulty determining the appropriate timing, sequence, and dosages of administration for the drug, e.g., interferon-α, and the glucocorticoid blocker.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts and esters" refers to salts and esters that are acceptable for use in pharmaceutical formulations and have the desired pharmacological properties. Such salts may include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester may be a mono-acid-mono-salt or ester or a di-salt or ester; and similarly where there are more than two acidic groups present, some or all of such groups can be salified or esterified. Compounds named in this invention may be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stercoisomeric form, and the naming of such compounds is intended to include all single stereoisomers and all mixtures (whether racemic or otherwise) of such stereoisomers.

A "second therapeutic agent" refers to any drug that can used to treat a patient suffering from psychosis associated with interferon-α therapy. For example, the second therapeutic agent may be a drug administered to treat psychosis, e.g., an antipsychotic agent. The second therapeutic agent may also be a drug administered to treat one of the other side effects associated with interferon-α therapy, e.g., depression. The second therapeutic agent may also be a drug administered to treat the initial condition or disease warranting interferon-α therapy. For example, the second therapeutic agent may be ribavarin, a drug typically administered in combination with interferon-α therapy to treat Hepatitis C. The second therapeutic agent may also be a drug used to treat a secondary condition suffered by the patient.

A "therapeutically effective amount" means the amount that, when administered to a patient for treating psychosis, is sufficient to effect treatment for that disease. In the case of a therapeutically effective amount of an antiglucocorticoid for ameliorating the symptoms of psychosis in a patient, the therapeutically effective amount of the antiglucocorticoid will be an amount necessary to ameliorate the symptoms of psychosis in the patient. The response can be measured by an improved mental well-being of the patient.

DETAILED DESCRIPTION OF THE INVENTION

Introduction

The present invention provides a method for reducing the side effects associated with interferon-α therapy. In particular, the invention provides a method for ameliorating the symptoms of psychosis associated with interferon α therapy. The present invention is based in part, on the discovery that patients suffering from psychosis associated with interferon-α treatment have glucocorticoid regulatory dysfunction and can be successfully treated with antiglucocorticoid therapy.

There are multiple possible mechanisms by which interferon may cause neuropsychiatric side effects, including psychosis. Given the variety of psychiatric syndromes associated with interferon α therapy and the fact that not all psychotic syndromes are amenable to antiglucocorticoid treatment, e.g., schizophrenia, it is surprising that psychosis associated with interferon-α treatment is treatable by the administration of glucocorticoid receptor antagonists.

Cortisol acts by binding to an intracellular, glucocorticoid receptor (GR). In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

The biologic effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions, which, by binding to GR, block the ability of an agonist to effectively bind to and/or activate the GR. One family of known GR antagonists, mifepristone and related compounds, are effective and potent anti-glucocorticoid agents in humans (Bertagna, *J. Clin. Endocrinol. Metab.* 59:25, 1984). Mifepristone binds to the GR with high affinity, with a K of dissociation $<10^{-9}$ M (Cadepond, *Annu. Rev. Med.* 48:129, 1997). Thus, in one embodiment of the invention, mifepristone and related compounds are used to treat patients suffering from psychosis associated with interferon-α treatment.

As the methods of the invention include use of any means to inhibit the biological effects of an agonist-bound GR, illustrative compounds and compositions which can be used to treat patients suffering from psychosis associated with interferon-α treatment are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. Diagnosis of Psychosis in Patients Undergoing Interferon Therapy

The present invention pertains to the discovery that agents that can inhibit a biological response caused by an agonist-occupied glucocorticoid receptor are effective for ameliorating psychosis associated with interferon-α therapy.

A number of tests, including objective tests, can be used to determine whether an individual suffering from a disease or condition treatable by interferon-α therapy is a candidate for treatment using the methods of the present invention. A candidate for treatment is an individual who, at some point during the course of interferon-α therapy, exhibits symptoms of psychosis. Typically, the patient will have no prior history of psychosis. Tests that can be used to determine whether an individual is exhibiting symptoms of psychosis include, for example, tests measuring changes in cognitive ability of the patient.

Psychosis associated with interferon-α therapy may be manifest as a mental illness in the form of a syndrome, or as an element of a variety of disease processes. There are various means to diagnose these various forms of psychosis and assess the success of treatment. These means include classical psychological evaluations in addition to various laboratory procedures. Such means are well-described in the scientific and patent literature, and some illustrative examples are provided below.

a. Assessing and Diagnosing Psychosis

While the practitioner can use any set of proscribed or empirical criteria to diagnose the presence of a psychosis associated with interferon-c therapy as an indication to practice the methods of the invention, some illustrative diagnostic guidelines and examples of relevant symptoms and conditions are described below.

Psychosis can be diagnosed by formal psychiatric assessment using, for example, a semi-structured clinical interview described as "The Structured Clinical Interview for DSM-II-R, or "SCID." SCID is designed to be administered by clinicians and researchers familiar with the diagnostic criteria used in the DSM-II-R (the revised third edition of DSM). The SCID has two parts, one for Axis I disorders (clinical disorders and other conditions that may be a focus of clinical attention) and another for Axis II personality disorders (personality disorders and mental retardation) (see DSM-IV, supra, pgs 25-31, for a general description of a "multiaxial assessment system" to guide clinicians in planning treatment and predicting outcome). At the start of the SCID interview, an overview of the present illness, chief complaint, and past episodes of major psychopathology are obtained before systematically asking the patient questions about specific symptoms. The interview schedule itself has many questions which are open-ended so that patients have an opportunity to describe symptoms in their own words.

At the conclusion of the interview, the interviewer also completes the Global Assessment of Functioning (GAF) scale, the fifth ("V") Axis on DSM-IV's multiaxial assessment system. Axis V is for reporting the clinician's judgment of the individual's overall level of functioning. This information is useful in planning treatment and measuring its impact, and in predicting outcome. The GAF scale is particularly useful in tracking the clinical progress of individuals in global terms using a single measure (see DSM-IV, supra, pages 30 to 31; Kaplan, ed. (1995), supra). In some settings, it may be useful to assess social and occupational disability and to track progress in rehabilitation independent of the severity of the psychological symptoms. For this purpose, use, for example, the proposed Social and Occupational Functioning Assessment Scale (SOFAS) DSM-IV, supra, pg. 760, Appendix B. Additional assessment schemes can be used, for example, the Global Assessment of Relational Functioning (GARF) Scale (DSM-IV, supra, pg 758, Appendix B) or the Defensive Functioning Scale (DSM-IV, supra, pg 751, Appendix B).

To assess the progress of a treatment for psychosis associated with interferon-α therapy or aid in its diagnosis or prognosis, the "Brief Psychiatric Rating Scale (BPRS)" can also be used after the semistructured interview with the patient. The BPRS is an 18-dimension rating scale. Each dimension represents a domain of behavior and psychiatric symptoms, such as anxiety, hostility, affect, guilt and orientation. These are rated on a seven-point "Likert Scale" from "not present" to "extremely severe." The BPRS is brief, easily learned and provides a quantitative score that reflects global pathology. The BPRS is useful in providing a crude barometer of a patient's overall benefit from treatment, and thus is useful in assessing changes in an individual's condition after treatment and amelioration using the methods of the invention (Overall (1962) Psychol. Rep. 10:799; Kaplan (1995), supra).

Objective tests can be also be used with these subjective, diagnostic criteria to determine whether an individual is suffering from psychosis associated with interferon-α therapy and to measure and assess the success of a particular treatment schedule or regimen. Diagnosis, categorization, or assessment of treatment of psychosis or any psychiatric condition can be objectively assessed using any test known in the art, such as that described by Wallach (1980) J. Gerontol. 35:371-375, or the Stroop Color and Word Test. The so-called "Wallach Test" can measure the presence and degree of psychosis by evaluating cognitive changes in the individual. The test assesses recognition memory, as described above.

The Stroop Color and Word Test ("Stroop Test") is another means to objectively determine whether an individual is suffering from psychosis associated with interferon-α therapy and to measure efficacy of treatment (see Golden, supra). The Stroop Test can differentiate between individuals with psychosis and those without. Briefly, the test developed from the observation that the naming of colors is always slower than the reading of color names in literate adults. For instance, it always takes less time to read the printed word "yellow" than it does to recognize what color a word is printed in (for example, "XXX" printed in yellow ink). Furthermore, if color words are printed in non-matching colored inks (as, the word yellow in red ink), it takes a normal individual 50% longer to name the proper color (red) than if they are shown only the color (such as a red rectangle, or "XXX" in red). This delay in color recognition is called "the color-word interference effect" and is the time is the variable parameter measured in the Stroop Test. The greater the delay, the lower the Stroop Test score (see also Uttl (1997) J. Clin. Exp. Neuropsychol. 19:405-420). Individuals with psychosis have statistically significantly lower scores on the Stroop Test than individuals without psychosis.

Psychiatric conditions associated with interferon-α therapy such as psychosis associated with interferon-α therapy, can be further diagnosed and evaluated using any of the many tests or criteria well-known and accepted in the fields of psychology or psychiatry for assessing and diagnosing psychiatric conditions.

The features (symptoms) of and criteria for diagnosing psychotic disorders, whether manifested as side effects of drug treatment, e.g., interferon-α therapy, or not, are further described in the DSM-IV, supra. While the practitioner can use any criteria or means to evaluate whether an individual is suffering from psychosis associated with interferon-α therapy to practice the methods of the invention, the DSM-IV sets forth a generally accepted standard for such diagnosing, categorizing and treating of psychiatric disorders, including psychosis manifested as a side effect of drug treatment. Psychosis is typically characterized as a mental disorder or condition causing gross distortion or disorganization of a person's mental capacity, affective response, and capacity to recognize reality, communicate, and relate to others to the degree of interfering with his capacity to cope with the ordinary demands of everyday life. In a condition or illness involving psychosis, delusions or hallucinations can be present. The content of the delusions or hallucinations have many depressive themes. In psychotic major depression there can be "mood-congruent" psychotic features, including, for example, delusions of guilt, delusions one deserves punishment (e.g. because of a personal inadequacy or moral transgression), nihilistic delusions (e.g. of world or personal destruction), somatic delusions (e.g. having cancer), or delusions of poverty. Hallucinations, when present in psychotic major depression are usually transient and not elaborate and may involve voices that berate the patient for shortcomings or sins. More rarely, the content of the delusions or hallucinations has no apparent relationship to depressive themes. In this situation these "mood-incongruent" psychotic features include, for example, grandiose delusions (See U.S. Pat. No. 6,150,349).

2. General Laboratory Procedures

When practicing the methods of the invention, a number of general laboratory tests can be used to assist in the diagnosis, progress and prognosis of the patient with catatonia, including monitoring of parameters such as blood cortisol, drug metabolism, brain structure and function and the like. These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol have been associated with catatonia, although the invention may also be practiced upon patients with apparently normal levels of blood cortisol.

Thus, monitoring blood cortisol and determining baseline cortisol levels are useful laboratory tests to aid in the diagnosis, treatment and prognosis of a catatonia patient. A wide variety of laboratory tests exist that can be used to determine whether an individual is normal, hypo- or hypercortisolemic. Catatonia patients typically have normal levels of cortisol that are often less than 25 µg/dl in the morning, and frequently about 15 µg/dl or less in the afternoon, although the values often fall at the high end of the normal range, which is generally considered to be 5-15 µg/dl in the afternoon.

Immunoassays such as radioimmunoassays are commonly used because they are accurate, easy to do and relatively cheap. Because levels of circulating cortisol are an indicator of adrenocortical function, a variety of stimulation and suppression tests, such as ACTH Stimulation, ACTH Reserve, or dexamethasone suppression (see, e.g., Greenwald, *Am. J. Psychiatry* 143:442-446, 1986), can also-provide diagnostic, prognostic or other information to be used adjunctively in the methods of the invention.

One such assay available in kit form is the radioimmunoassay available as "Double Antibody Cortisol Kit" (Diagnostic Products Corporation, Los Angeles, Calif.), (*Acta Psychiatr. Scand.* 70:239-247, 1984). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor predilution. This assay is described in further detail in Example 2, below.

b. Determination of Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat catatonia, an illustrative example of determining blood and urine mifepristone levels is set forth in the Example below.

c. Other Laboratory Procedures

Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai *Pharmacol. and Experimental Therapeutics* 241:401-406, 1987.

3. Glucocorticoid Receptor Antagonists to Treat Patients Undergoing Interferon Therapy The invention provides methods for treating psychosis associated with interferon-α therapy utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below A. Steroidal Anti-Glucocorticoids as GR Antagonists.

Steroidal glucocorticoid antagonists are administered for treating psychosis associated with interferon-α therapy in a patient in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre, *J. Steroid Biochem.* 33:557-563, 1989).

Examples of steroidal GR antagonists include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, and 5,696,127. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylamninoethoxyphenyl)-17α-propynyl-17β-hydroxy-4,9-estradien-3-one (RU009), and 17β-hydroxy-17α-19-(4-methylphenyl)androsta-4,9(11)-dien-3-one (RU044).

1. Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. Ibid). Preferred embodiments of the invention include all 11-beta-aryl steroid backbone derivatives because these compounds are devoid of progesterone receptor (PR) binding activity (Agarwal *FEBS* 217:221-226, 1987). Another. preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 11-beta phenyl-aminodimethyl steroid, the steroid receptor is maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-beta-hydrox-11-beta-(4-dimethyl-aminophenyl)17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)-17-alpha-(propynyl-17 beta-hydroxy-4,9-estradien-3-one) (see Bocquel, *J. Steroid Biochem. Molec. Biol.* 45:205-215, 1993). Another GR antagonist related to RU486 is RU044 (RU43.044) 17-beta-hydrox-17-alpha-19-(4-methyl-phenyl)-androsta-4,9 (11)-dien-3-one) (Bocquel, 1993, supra). See also Teutsch, *Steroids* 38:651-665, 1981; U.S. Pat. Nos. 4,386,085 and 4,912,097.

One embodiment includes compositions containing the basic glucocorticoid steroid structure which are irreversible anti-glucocorticoids. Such compounds include alpha-keto-methanesulfonate derivatives of cortisol, including cortisol-21-mesylate (4-pregnene-11-beta, 17-alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons, *J. Steroid Biochem.* 24:25-32 1986; Mercier, *J. Steroid Biochem.* 25:11-20, 1986; U.S. Pat. No. 4,296,206.

2, Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, *Nature* 279:158-160, 1979).

3, Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoid activity in comparison to 17-propinyl side chain containing compounds.

Additional glucocorticoid receptor antagonists known in the art and suitable for practice of the invention include 21-hydroxy-6,19-oxidoprogesterone (see Vicent, *Mol. Pharm.* 52:749-753, 1997), Org31710 (see Mizutani, *J Steroid Biochem Mol Biol* 42(7):695-704, 1992), RU43044, RU40555 (see Kim, *J Steroid Biochem Mol Biol.* 67(3):213-22, 1998), RU28362, and ZK98299.

B. Non-Steroidal Anti-Glucocorticoids as Antagonists

Non-steroidal glucocorticoid antagonists are also used in the methods of the invention to treat psychosis associated with interferon-α therapy. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour, *Int. J. Pept. Protein Res.* 43:297-304, 1994; de Bont, *Bioorganic & Medicinal Chem.* 4:667-672, 1996). The creation and simultaneous screening of large libraries of synthetic molecules can be carried out using well-known techniques in combinatorial chemistry, for example, see van Breemen, *Anal Chem.* 69:2159-2164, 1997; and Lam, *Anticancer Drug Des* 12:145-167, 1997, Design of peptidomimetics specific for GR can be designed using computer programs in conjunction with combinatorial chemistry (combinatorial library) screening approaches (Murray, *J. of Computer-Aided Molec. Design* 9:381-395, 1995; Bohm, *J. of Computer-Aided Molec. Design* 10:265-272, 1996). Such "rational drug design" can help develop peptide isomerics and conformers including cycloisomers, retro-inverso isomers, retro isomers and the like (as discussed in Chorev, *TibTech* 13:438-445, 1995).

Examples of non-steroidal GR antagonists include ketoconazole, clotrimazole; N-(triphenylmethyl)imidazole; N-([2-fluoro-9-phenyl]fluorenyl)imidazole; N-([2-pyridyl]diphenylmethyl)imidazole; N-(2-[4,4',4"-trichlorotrityl]oxyethyl)morpholine; 1-(2[4,4',4"-trichlorotrityl]oxyethyl)-4-(2-hydroxyethyl)piperazine dimaleate; N-([4,4',4"]-trichlorotrityl)imidazole; 9-(3-mercapto-1,2,4-triazolyl)-9-phenyl-2,7-difluorofluorenone; 1-(2-chlorotrityl)-3,5-dimethylpyrazole; 4-(morpholinomethyl)-A-(2-pyridyl)benzhydrol; 5-(5-methoxy-2-(N-methylcarbamoyl)-phenyl)dibenzosuberol; N-(2-chlorotrityl)-1-prolinol acetate; 1-(2-chlorotrityl)-2-methylimidazole; I -2-chlorotrityl)-1,2,4-triazole; 1,S-bis(4,4',4"-trichlorotrityl)-1,2,4-triazole-3-thiol; and N-((2,6-dichloro-3-methylphenyl)diphenyl)methylimidazole (see U.S. Pat. No. 6,051,573); the GR antagonist compounds disclosed in U.S. Pat. No. 5,696,127; the glucocorticoid-receptor antagonists disclosed in Bradley et al., *J. Med. Chem.* 45, 2417-2424 (2002), e.g., 4a(S)-Benzyl-2(R)-chloroethynyl-1,2,3,4,4a,9,10,10a(R)-octahydro-phenanthrene-2,7-diol ("CP 394531") and 4a(S)-Benzyl-2(R)-prop-1-ynyl-1,2,3,4,4a,9,10,10a(R)-octahydro-phenanthrene-2,7-diol ("CP 409069") and related compounds disclosed in PCT International Application No. WO 00/66522; the compound (11b,17b)-11-(1,3-benzo-dioxol-5-yl)-17-hydroxy-17-(1 -propynyl)estra-4,9-dien-3-one("ORG 34517") disclosed in Hoyberg et al., *Int'l J. of Neuro-psychopharmacology,* 5:Supp. 1, S148 (2002); the compounds disclosed in PCT International Application No. WO 96/19458, which describes non-steroidal compounds which are high-affinity, highly selective antagonists for steroid receptors, such as 6-substituted-1,2-dihydro-N-protected-quinolines; benzopyrano[3,4-f]quinolones described as glucocorticoid receptor modulators disclosed in PCT International Application No. WO 99/41256 and WO 02/02565; dibenzopyrans disclosed as glucocorticoid receptor antagonists in PCT International Application No. WO 01/16128; aminobenzene derivatives disclosed as glucocorticoid receptor modulators in PCT International Application No. WO 02/064550; some κ opioid ligands, such as the κ opioid compounds dynorphin-1,13-diamide, U50,488 (trans-(1R,2R)-3,4-dichloro-N-methyl-N-[2-(1-pyrrolidinyl)cyclohexyl]benzeneacetamide), bremazocine and ethylketocyclazocine; and the non-specific opioid receptor ligand, naloxone, as disclosed in Evans et al., *Endocrin.,* 141:2294-2300 (2000); the compound (3,5-dibromo-4-[5-isopropyl-4-methoxy-2-(3-methylbenzoyl-phenoxy]phenyl)acetic acid ("KB285") disclosed in PCT International Application No. WO 99/63976 and related compounds disclosed in PCT International Application No. WO 01/47959, 02/43648 and 02/44120.

C. Identifying Specific Glucocorticoid Receptor Antagonists

Because any specific GR antagonist can be in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner, *Meth. Enzymol.* 15:633, 1970, This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany, *Biochem. Biophys. Acta* 886:162-168, 1986).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi, et al., *Steroids* 57:313-318, 1992). As another example, the ability of a putative GR antagonist to block nuclear binding of $^3$H-dexamethasone-GR complex can be used (Alexandrova et al., *J. Steroid Biochem. Mol. Biol.* 41:723-725, 1992). To further identify putative GR antagonists, kinetic assays able to discriminate between glucocorticoid agonists and antagonists by means of receptor-binding kinetics can also be used (as described in Jones, *Biochem J.* 204:721-729, 1982).

In another illustrative example, the assay described by Daune, *Molec. Pharm.* 13:948-955, 1977; and in U.S. Pat. No. 4,386,085, can be used to identify anti-glucocorticoid activity. Briefly, the thymocytes of surrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos. 4,296,206 (see above); 4,386,085 (see above); 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

The specificity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606, 021; 5,696,127; 5,215,916; 5,071,773). Such an analysis can be perfomied using either direct binding assay or by assessing competitive binding to the purified GR or MR in the presence of a known antagonist. In an exemplary assay, cells that are stably expressing the glucocorticod receptor or mineralocorticoid receptor (see, e.g., U.S. Pat. No. 5,606,021) at high levels are used as a source of purified receptor. The affinity of the antagonist for the receptor is then directly measured. Those antagonists that exhibit at least a 100-fold higher affinity, often 1000-fold, for the GR relative to the MR are then selected for use in the methods of the invention.

A GR-specific antagonist may also be defined as a compound that has the ability to inhibit GR-mediated activities, but not MR-mediated activities. One method of identifying such a GR-specific antagonist is to assess the ability of an antagonist to prevent activation of reporter constructs using transfection assays (see, e.g., Bocquel et al, *J. Steroid Biochem Molec. Biol.* 45:205-215, 1993, U.S. Pat. Nos. 5,606, 021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. A GR-specific-antagonist is considered to exhibit at least a 100-fold, often 1000-fold or greater, activity towards the GR relative to the MR.

4, Treating a Patient Undergoing Interferon Therapy Using Glucocorticoid Receptor Antagonists Antiglucocorticoids, such as mifepristone, are formulated as pharmaceuticals to be used in the methods of the invention. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

A. Glucocorticoid Receptor Antagonists as Pharmaceutical Compositions

The GR antagonists used in the methods of the invention can be administered by any means known in the art, e.g., parenterally, topically, orally, or by local administration. such as by aerosol or transdermally. The methods of the invention provide for prophylactic and/or therapeutic treatments. The GR antagonists as pharmaceutical formulations can be administered in a variety of unit dosage forms depending upon the condition or disease and the degree of psychosis, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's"). Therapeutically effective amounts of glucocorticoid blockers suitable for practice of the method of the invention may range from about 0.5 to about 25 milligrams per kilogram (mg/kg). A person of ordinary skill in the art will be able without undue experimentation, having regard to that skill and this disclosure, to determine a therapeutically effective amount of a particular glucocorticoid blocker compound for practice of this invention.

In general, glucocorticoid blocker compounds may be administered as pharmaceutical compositions by any method known in the art for administering therapeutic drugs. Compositions may take the form of tablets, pills, capsules, semi-solids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso AR: Remington's Pharmaceutical Sciences, 17th ed., Mack Publishing Company, Easton Pa., 1985, Suitable liquid carriers, especially for injectable solutions, include water, aqueous saline solution, aqueous dextrose solution, and glycols.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997, The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Glucocorticoid blocker pharmaceutical formulations can be prepared according to any method known to the art for the manufacture of pharmaceuticals. Such drugs can contain sweetening agents, flavoring agents, coloring agents and preserving agents. Any glucocorticoid blocker formulation can be admixtured with nontoxic pharmaceutically acceptable excipients which are suitable for manufacture.

Typically, glucocorticoid blocker compounds suitable for use in the practice of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the glucocorticoid blocker compounds, preferably 0.00001% w to 1% w, with the remainder being the excipient or excipients. For example, the GR antagonist mifepristone is given orally in tablet form, with dosages in the range of between about 0.5 and 25 mg/kg, more preferably between about 0.75 mg/kg and 15 mg/kg, most preferably about 10 mg/kg.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Pharmaceutical preparations for oral use can be obtained through combination of glucocorticoid blocker compounds with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermal injection of drug (e.g., mifepristone)-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J Pharm. Pharmacol.* 49:669-674, 1997). Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5, that is combined with buffer prior to use In another embodiment, the GR antagonist formulations of the invention are useful for parenteral administration, such as intravenous (IV) administration. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein-receptors of the cell resulting in endocytosis. By using liposomes, particularly where the liposome surface carries ligands specific for target cells, or are otherwise preferentially directed to a specific organ, one can focus the delivery of the GR antagonist-into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

A pharmaceutical composition of the invention may optionally contain, in addition to a glucocorticoid blocker compound, interferon-α. The pharmaceutical composition may also optionally contain, in addition to the glucocorticoid blocker compound and interferon-α, at least one other therapeutic agent, e.g., a therapeutic agent useful for the treatment of the side effects associated with interferon-α therapy or for the treatment of the disease in the patient warranting interferon-α therapy. For example, the pharmaceutical composition may contain mifepristone, interferon-α, and ribavarin for the treatment of Hepatitis C in a patient.

B. Determinig Dosing Regimens for Glucocorticoid Receptor Antagonists

The methods of the invention ameliorate psychosis associated with interferon-α therapy, i.e., prevent, slow the onset of, decrease the frequency of, diminish the severity of or cure psychosis associated with interferon-α therapy and/or its complications. The amount of GR antagonist adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the psychosis. For example, a typical preferred pharmaceutical formulation for oral administration of mifepristone would be about 5 to 15 mg/kg of body weight per patient per day, more preferably between about 8 to about 12 mg/kg of body weight per patient per day, most preferably 10 mg/kg of body weight per patient per day, although dosages of between about 0.5 to about 25 mg/kg of body weight per day maybe used in the practice of the invention. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

After a pharmaceutical comprising a GR antagonist of the invention has been formulated in a acceptable carrier, it can be placed in an appropriate container and labeled for treatment with interferon-α. For administration of GR antagonists, such labeling would include, e.g., instructions concerning the amount, frequency and method of administration.

C. Concomitant Administration of Antiglucocorticoids with Interferon-α and/or Other Therapeutic Agents The antiglucocorticoids of the present invention are used to treat patients suffering from psychosis associated with interferon-α therapy. Typically, an antiglucocorticoid will be administered in combination with interferon-α therapy. Methods of administering interferon-α to a patient suffering from a disease treatable by interferon-α are well known and can be found in Goodman & Gilman's, The Pharmacological Basis of Therapeutics, Ninth Edition and Harrison's Principles of Internal Medicine, 14th Edition and are thus not described in detail. Diseases amenable to interferon-α therapy are also well known to the skilled practitioner. They include, but are not limited to, cancer, chronic hepatitis, acute hepatitis, chronic myeloid leukemia, HTLV (Human T-Cell Lymphotropic Virus), lupus-like reaction, melanoma, renal cancer, HIV, AIDS and other viral infections. For example, in some embodiments of the present invention, the patient will be suffering from psychosis associated with interferon-α therapy administered to treat Hepatitis C in the patient. The state of the art allows the clinician to determine the interferon-α dosage regimen for each individual patient and disease or condition treated to determine correct dosage. For example, antiviral therapy with interferon-α for a patient suffering from Hepatitis C is recommended at a dosage of 3 million units administered subcutaneously three times weekly for about 6 to 12 months. (National Institutes of Health Consensus Development Conference panel (1997) Management of Hepatitis C. *Hepatology* 26(3 Suppl 1):2S-10S).

When antiglucocorticoids are administered concomitantly with interferon-α therapy, the symptoms of psychosis associated with interferon-α therapy will be diminished in the patient. The antiglucocorticoid will be administered at such times that both the antiglucocorticoid and interferon-α reach a therapeutically effective amount in the patient. In a preferred embodiment, interferon-α and the antiglucocorticoid, e.g., mifepristone, will be administered contemporaneously, e.g., at the same time throughout the course of interferon-α treatment. In other embodiments, the antiglucocorticoid may be administered for only a subset of the interferon-α therapy, e.g., only during the time that the patient exhibits symptoms of psychosis. The skilled practitioner will be able to determine, using the methods of the present invention, if antiglucocorticoid therapy is necessary throughout the course of interferon-α therapy, e.g., by administering the BPRS test as described above. The dosage schedule and amounts used will depend upon a variety of factors, including the severity of the psychosis in the patient, the general state of the patient's health, the patient's physical status, age and the like.

In some embodiments of the present invention, the antiglucocorticoid will be administered concomitantly with interferon-α and a second therapeutic agent. A skilled practitioner will determine whether the patient's condition can be further ameliorated by a second or third or fourth therapeutic agent. In a preferred embodiment, the second therapeutic agent will be ribavirin and will be administered in combination with interferon-α to treat Hepatitis C. The second therapeutic agent may also a drug useful for treating the various side effects associated with interferon-α therapy, e.g., psychosis, depression, cognitive disorders and suicidal tendencies. The second therapeutic agent may also be a drug used to treat either the disease or condition warranting the interferon-α therapy or an associated or non-associated disease or condition of the patient. Any number of therapeutic agents can be administered with the antiglucocorticoid in the methods of the present invention.

5, Glucocorticoid Blocker Kits

After a pharmaceutical comprising a glucocorticoid blocker has been formulated in a suitable carrier, it can be placed in an appropriate container and labeled for treatment of an indicated disease, e.g., psychosis associated with interferon-α therapy. In some embodiments, the container may contain both interferon-α and an antiglucocorticoid blocker and be labeled for treatment of any disease treatable by interferon-α therapy, e.g., Hepatitis C. Additionally, a third pharmaceutical comprising at least one other therapeutic agent useful in the treatment of the patient suffering from a disease treatable by interferon-α therapy will be placed in the container as well, and labeled for treatment of the indicated disease. Alternatively, a single pharmaceutical comprising a glucocorticoid blocker and interferon-α can be placed in an appropriate container and labeled for treatment of an indicated disease. For administration of pharmaceuticals comprising glucocorticoid blockers and of pharmaceuticals comprising, in a single pharmaceutical, glucocorticoid blockers and interferon-α, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

In one embodiment, the invention provides for a kit for the treatment of Hepatitis C, which includes a glucocorticoid blocker and instructional materials teaching the indications, dosage, and schedule of administration of the glucocorticoid blocker. When mifepristone is the glucocorticoid blocker provided in the kit, the instructional material indicates that the glucocorticoid blocker can be used in a daily amount of about 8 to 12 mg/kg of body weight per day, and the administration of the glucocorticoid blocker continues for a period of about four days. In another embodiment, the invention provides for a kit for the treatment of Hepatitis C, which includes a glucocorticoid blocker and interferon-α with instructions materials teaching the indications, dosage, and schedule of administration of the glucocorticoid blocker and interferon-α.

It is understood that the examples and embodiments described herein are for illustrative purposes only and that various modifications or changes in light thereof will be suggested to persons skilled in the art and are to be included within the spirit and purview of this application and scope of the appended claims.

All publications and patent applications cited in this specification are herein incorporated by reference as if each individual publication or patent application were specifically and individually indicated to be incorporated by reference.

EXAMPLES

Example 1

Treating Psychosis Associated with Interferon-α Therapy with Mifepristone

Patients undergoing interferon-α therapy exhibiting symptoms of psychosis are diagnosed with psychosis using subjective and objective criteria, including criteria as set forth by the DSM-IV as described above.

The glucocorticoid receptor antagonist, mifepristone, is used to treat patients undergoing interferona therapy and exhibiting symptoms of psychosis. Mifepristone is administered in dosages of 200 mg daily during the course of interferon-α therapy. Dosages are adjusted if necessary and further evaluations are performed periodically throughout treatment. To delineate and assess the effectiveness of mifepristone in ameliorating the symptoms of psychosis, formal psychiatric tests and assessments are administered to the patient. These tests and diagnostic assessments take place at baseline (patient's entry into treatment) and periodically throughout treatment.

What is claimed is:

1. A method of ameliorating the symptoms of psychosis associated with interferon α therapy in a patient, comprising:
administering to the patient having received interferon α therapy and suffering from psychosis associated with the interferon α therapy, an amount of a glucocorticoid receptor antagonist effective to ameliorate the symptoms of psychosis in the patient, with the proviso that the patient is not otherwise in need of treatment with a glucocorticoid receptor antagonist.

2. The method of claim 1, wherein the glucocorticoid receptor antagonist comprises a steroidal skeleton with at least one phenyl-containing moiety in the 11-beta position of the steroidal skeleton.

3. The method of claim 2, wherein the phenyl-containing moiety in the 11-beta position of the steroidal skeleton is a dimethylaminophenyl moiety.

4. The method of claim 3, wherein the glucocorticoid receptor antagonist comprises mifepristone.

5. The method of claim 3 wherein the glucocorticoid receptor antagonist is selected from the group consisting of 11-β-(4-dimethyl-aminoethoxyphenyl)-17α-propynyl-17β-hydroxy-4,9-estradien-3-one, and 17β-hydrox-17α-19-(4-methyl-phenyl)androsta -4,9 (11)-dien-3-one.

6. The method of claim 1 wherein the glucocorticoid receptor antagonist is selected from the group consisting 4α(S)-Benzyl-2(R)-prop-1-ynyl -1,2,3,4,4α,9,10,10a(R)-octahydro-phenanthrene-2,7-diol and 4α(S)-Benzyl-2(R)-chloroethynyl -1,2,3,4,4α,9,10,10a(R)-octahydro-phenanthrene-2,7-diol.

7. The method of claim 1, wherein the glucocorticoid receptor antagonist is (11β,17β)-11-(1,3-benzodioxo-5-yl)-17-hydroxy-17-(1-propynyl)estra-4,9-dien-3-one.

8. The method of claim 1, wherein the glucocorticoid receptor antagonist is administered to the patient concomitantly with interferon-α.

9. The method of claim 8, wherein the glucocorticoid receptor antagonist is administered to the patient throughout the course of interferon-α therapy.

10. The method of claim 8, wherein the glucocorticoid receptor antagonist is administered to the patient concomitantly with interferon-α and a second therapeutic agent.

11. The method of claim 10, wherein the second therapeutic agent is an anti-viral agent.

12. The method of claim 11, wherein the anti-viral agent is ribavirin.

13. The method of claim 1, wherein the glucocorticoid receptor antagonist is administered in a daily amount of between about 0.5 to about 25 mg per kilogram of body weight per day.

14. The method of claim 13, wherein the glucocorticoid receptor antagonist is administered in a daily amount of between about 1 to about 4 mg per kilogram of body weight per day.

15. The method of claim 1, wherein the mode of administration is selected from the group consisting of oral administration, transdermal application, nebulized suspension, and aerosol spray.

16. The method of claim 1, wherein the patient is suffering from a viral infection caused by a virus selected from the group consisting of hepatitis C virus, hepatitis B virus, and hepatitis D virus.

17. The method of claim 16, wherein the viral infection is acute or chronic.

18. The method of claim. 1, wherein the patient is suffering from chronic myelogenous leukemia, HIV, Human T-Cell Lymphotropic Virus or cancer.

19. The method of claim 1, wherein the patient has a history of substance abuse.

* * * * *